United States Patent
Stjern et al.

(10) Patent No.: US 9,435,748 B2
(45) Date of Patent: Sep. 6, 2016

(54) DETECTION OF CONTAMINATED AREAS

(71) Applicant: SPÅRAB PRODUKTER AB, Ängelholm (SE)

(72) Inventors: Per Anders Stjern, Åstorp (SE); Tobias Halthur, Malmö (SE)

(73) Assignee: SPÅRAB PRODUKTER AB, Ängelholm (SE)

( * ) Notice: Subject to any disclaimer, the term of this patent is extended or adjusted under 35 U.S.C. 154(b) by 0 days.

(21) Appl. No.: 14/373,619

(22) PCT Filed: Jan. 21, 2013

(86) PCT No.: PCT/SE2013/050035
§ 371 (c)(1),
(2) Date: Jul. 21, 2014

(87) PCT Pub. No.: WO2013/112098
PCT Pub. Date: Aug. 1, 2013

(65) Prior Publication Data
US 2014/0361195 A1    Dec. 11, 2014

(30) Foreign Application Priority Data

Jan. 27, 2012  (SE) ...................................... 1250056

(51) Int. Cl.
| | | |
|---|---|---|
| *G01N 21/94* | (2006.01) | |
| *G01N 21/91* | (2006.01) | |
| *G03F 1/82* | (2012.01) | |
| *G03F 7/20* | (2006.01) | |
| *G01N 21/64* | (2006.01) | |
| *G03F 1/84* | (2012.01) | |
| *G01N 21/47* | (2006.01) | |

(52) U.S. Cl.
CPC .......... *G01N 21/94* (2013.01); *G01N 21/6447* (2013.01); *G01N 21/91* (2013.01); *G01N 21/47* (2013.01); *G01N 21/64* (2013.01); *G01N 2021/646* (2013.01); *G03F 1/82* (2013.01); *G03F 1/84* (2013.01); *G03F 7/707* (2013.01); *G03F 7/7085* (2013.01); *G03F 7/70566* (2013.01); *G03F 7/70916* (2013.01)

(58) Field of Classification Search
CPC combination set(s) only.
See application file for complete search history.

(56) References Cited

U.S. PATENT DOCUMENTS

| | | | |
|---|---|---|---|
| 3,527,709 A | * | 9/1970 | Alburger ................ C09K 11/06 250/302 |
| 4,651,010 A | | 3/1987 | Javan |
| 4,858,465 A | | 8/1989 | Molina |
| 4,867,796 A | * | 9/1989 | Asmus et al. .................... 134/1 |
| 5,191,803 A | | 3/1993 | Gamache |
| 5,225,675 A | | 7/1993 | O'Donnell |
| 2002/0034825 A1 | | 3/2002 | Schweigart |
| 2002/0142473 A1 | | 10/2002 | Lagraff et al. |
| 2002/0180992 A1 | | 12/2002 | Borchardt et al. |
| 2005/0037501 A1 | | 2/2005 | Meyer et al. |
| 2009/0237645 A1 | | 9/2009 | Hamby et al. |
| 2010/0291685 A1 | | 11/2010 | Zhang |

FOREIGN PATENT DOCUMENTS

| | | |
|---|---|---|
| DE | 198 46 775 A1 | 4/2000 |
| DE | 10217950 | 11/2002 |
| DE | 102006029485 | 1/2008 |
| WO | WO-0022421 | 4/2000 |
| WO | WO-0039566 | 7/2000 |
| WO | WO-03025555 | 3/2003 |
| WO | WO-2009005144 | 1/2009 |

OTHER PUBLICATIONS

International Search Report mailed Jun. 4, 2013, from related international application No. PCT/SE2013/050035, six pages.
Extended European Search Report dated Sep. 17, 2015 for corresponding European Pat. No. 13741399.3.

* cited by examiner

*Primary Examiner* — Christine Sung
(74) *Attorney, Agent, or Firm* — Foley & Lardner LLP

(57) ABSTRACT

The present invention describes a method for the detection of contamination on a surface before performing a coating of the surface, said method comprising bringing a marker into contact with the surface, wherein the marker has the ability of accumulating at a contaminated area on the surface, and detecting the marker on the surface, wherein the marker is non-polar or amphiphilic.

6 Claims, No Drawings

DETECTION OF CONTAMINATED AREAS

CROSS-REFERENCE TO RELATED APPLICATIONS

The present application is a U.S. National Phase of International Patent Application No. PCT/SE2013/050035, filed Jan. 21, 2013, which claims priority from Swedish Patent Application No. 1250056-7, filed Jan. 27, 2012. The contents of these applications are incorporated herein by reference in their entirety.

FIELD OF THE INVENTION

The present invention relates to a method for the detection of contamination of a surface before the performance of a coating of the surface.

TECHNICAL BACKGROUND

There are methods today which are directed to detecting dirt on surfaces or quantifying the contamination degree on such surfaces. For instance in U.S. Pat. No. 5,828,460 there is disclosed a method for inspection of metallic surfaces before subsequent treatment thereof, such as painting. Several light sources are said to illuminate the inspected surface with light beams having different wave lengths, reflected radiation is detected and converted to electrical signals, the electrical signals are processed digitally, and the results of processing are displayed. Furthermore, methods like the one disclosed above are known to be used in e.g. the vehicle industry. In U.S. Pat. No. 6,320,654 there is e.g. disclosed a method of detecting selected surface defects of a vehicle body, the method comprising conveying a plurality of said vehicle bodies along a line of travel; irradiating sequential transverse sections of said vehicle bodies at selected angles with grid patterns of light; optically detecting reflective grid patterns of light from said transverse sections; processing data representing said reflective grid patterns, utilizing triangulation techniques and accounting for three-dimensional phase shifts, to generate composite detected data, comparing said composite data with selected reference data representing relevant defect surfaces of selected vehicles bodies and generating identification data representing coordinates of relevant defect surfaces of said vehicles bodies; and marking relevant defect surfaces on said vehicle bodies responsive to said coordinates of said identification data.

Likewise, in WO87/00629 there is disclosed a surface inspection apparatus for inspecting e.g. the paint surface of a motor car, the apparatus comprising laser means providing a beam of radiation, scanning means for scanning the beam across the surface, retro-reflective material being provided to reflect radiation reflected from the surface back along the incident beam path, the apparatus including the retro-reflective material being mounted as a unit to be moved over the surface of the motor car by means of a robot. Analysis of the light signal is said to indicate defects such as scratches, paint inclusions, orange peel, dry spray, dents and gloss defects.

Furthermore, in U.S. Pat. No. 5,844,801 there is disclosed a method of manufacturing of a vehicle body, the method comprising inter alia identifying a defective area of a surface by comparing a degree of surface distortion with a predetermined decision value, thereby determining whether said surface distortion is acceptable or not.

One aim of the present invention is to provide an improved method for detection of contamination on a surface, which method is very effective and still easy to use. Furthermore, the method according to the present invention is intended to effectively detect contaminants which are often found or used heavily today. Such examples are given below.

SUMMARY OF THE INVENTION

The stated purpose above is achieved by a method for the detection of contamination on a surface before performing a coating of the surface, said method comprising bringing a marker into contact with the surface, wherein the marker has the ability of accumulating at a contaminated area on the surface, and detecting the marker on the surface, wherein the marker is non-polar or amphiphilic. The expression "the marker has the ability of accumulating at a contaminated area" implies that the marker (or probe) associates to at least one contaminant present in the contaminated area.

A contaminated area is an area holding one or more substances (contaminants) of interest to detect. Such contaminants may e.g. be different kinds of oily substances, such as for instance lubricating oils used in all industry that glues, agglutinates, joins or seals. One example of such industry is the car industry. Other examples are different kinds of dirt, such as e.g. dust particles. Further examples are Teflon- and silicone based products, white grease, oil-based products, lubricants and release agents (i.e. chemicals that prevents penetration without mechanical influence) of all sorts.

In U.S. Pat. No. 4,858,465 there is disclosed a method for detecting and visually locating surface contaminants on an object, the method comprising applying to the surface of an object having a contaminant thereon, an aqueous contaminant locating composition which detects and indicates the presence of a contaminant on the surface of an object; removing excess contaminant locating composition from the surface of the object; applying an aqueous contaminant-identifier fluorescent developer onto the surface at the indicated contaminant; transferring by migration dye molecules to and associating same with the contaminant causing the contaminant to fluoresce; removing excess developer from the surface of the object; and viewing the surface of the object under lighting conditions to visually locate said surface contaminant. The contaminant identifier composition consists essentially of a fluorescent dye and a suitable carrier.

In U.S. Pat. No. 4,858,465 it is mentioned that contaminants if not detected and removed can prevent the penetrant inspection process from wetting the surfaces of parts and assemblies being inspected for defects such as cracks, and also prevent the paint and bonding processes from being effectively applied. It should, however, be said that the method according to U.S. Pat. No. 4,858,465 is direct to a detection method and not a coating procedure having an incorporated detection procedure. Moreover, when compared to the present invention, the method according to U.S. Pat. No. 4,858,465 involves the use of an aqueous contaminant locating composition, and not a marker being non-polar or amphiphilic, such as according to the present invention. Furthermore, the method according to U.S. Pat. No. 4,858,465 involves several steps which are not necessary or intended according to the present method.

It should be noted that the method according to the present invention may find use in many different technical applications, however it is specially related to varnishing applications, e.g. as a pre-treatment method before performing a painting/coating/varnishing, e.g. as a contaminant detection method performed before a car painting. Moreover, it should be understood that the method according to the present invention may be used as a method for determination of a clean surface suitable for a subsequent coating of said surface. The method is intended for detection of contaminants, and hence also as a security method for determination of a clean surface suitable for a subsequent coating. Furthermore, the expression "before performing a coating of the surface" should be interpreted as embodying all different kinds of possible coating techniques, such as painting, varnishing, and other kind of covering techniques, etc.

There are detecting methods used today in the car/vehicle industry. For instance in U.S. Pat. No. 6,320,654 there is disclosed a system for detecting selected surface defects of a vehicle body prior to painting, said system utilizing triangulation techniques and accounting for three-dimensional phase shifts to generate composite detected data, comparing such composite detected data with selected reference data to generate identification data representing coordinates of relevant defect surfaces, and marking relevant defect surfaces. It should be noted that a marking means may said to be involved in the system according to U.S. Pat. No. 6,320,654, but this is related to marking a defect surface with a marker substance, such as a water soluble marker substance, and not as marker used for associating to a contaminated area on the surface, and which subsequently is detected, such as according to the present invention.

SPECIFIC EMBODIMENTS OF THE INVENTION

Specific embodiments of the present invention are disclosed below. According to one embodiment of the present invention, the marker is a silicone tracer. Within the industry, there are very many articles being glued, joined together, painted or coated. If any silicone is contaminating a surface being intended for such use, no materials adhere properly to the surface. One large problem with silicone is that this substance is not detectable without the use of special means. Furthermore, both washing methods and mechanical methods for removal of silicone as a contaminant are insufficient.

Silicone is used in large quantities in the car industry, and as such, the method according to the present invention finds specific use in such car applications.

According to one specific embodiment of the present invention, the marker is fluorescent and the detection of the marker on the surface involves detection of fluorescence.

It should be noted that the use of fluorescence for detection reasons are known today. For instance in U.S.2009/0223635 there is disclosed a method quantifying a surface's cleanliness relative to a contaminant. The method is said to comprise the use a source of interrogating radiation to which the contaminant is responsive. Radiation emitted from the source is directed by a radiation means toward the surface or a surface cleaner that may hold the contaminant. A detector detects radiation from the surface or the surface cleaner produced in response to the interrogating radiation by the contaminant, e.g. fluorescent or phosphorescent radiation, and generate a corresponding signal that is compared by an analyzer relative to an electronic standard that corresponds to the surface in an acceptably clean state so as to quantify the surface's cleanliness. The method according to U.S.2009/0223635 does not involve the use of a marker. The method according to U.S.2009/0223635 may comprise a last step involving placing the surface in a contaminant sensitive environment, suitably being an oxygen facility, e.g. allowing the surface to be placed in contact with a halogen, e.g. fluorine. It should be noted that this halogen does not function as a marker, especially not as a marker being subsequently detected for associating to a contaminated surface.

It should further be noted that fluorescent materials are known for certain detection purposes today. For instance, GB573183 relates to the detection of faults in the surface of an article. The article is immersed in a fluorescent material, excess material is removed and the presence of fluorescence is thereafter used as a sign of faults, such as cracks, flaws, fissures, in the surface. The fluorescent material is however not used in a method comprising the use as a marker which is intended to associate to contaminated surfaces, and further involving the detection of the marker.

According to one specific embodiment of the present invention, the method involves the detection of fluorescence by applying ultraviolet light. In this sense it should be noted that different markers are possible to use according to the present invention, and they may interact differently with light. Many of the possible markers are excited by UV light, however some are excited also by visible light. Therefore, UV light may be used according to the present invention, however, also other detection means, such as other light sources, may be used depending on the marker solution used. It should be noted that the method according to the present invention also embodies detecting the association of the marker to the contaminant(s) of the surface without the use of such light sources.

Furthermore, as mentioned above, different markers may be used according to the present invention. Depending on the marker used, the concentration thereof, detection means etc. may vary. According to one specific embodiment of the present invention, the marker is non-polar or amphiphilic, where amphiphilic substances are such being composed of hydrophilic and hydrophobic parts. Hydrophobic or amphiphilic markers are enriched in oil stains and as such give an increased intensity in these oil areas. As such, they may be very interesting to use as markers according to the present invention. The association between the marker/probe and the contaminant(s) is according to the present invention driven by a hydrophobic interaction between the marker and the contaminant(s). This interaction is not a chemical binding as such.

Examples of interesting groups of markers according to the present invention are amphiphilic rhodamine or fluorescein derivatives, such as Octadecyl Rhodamine B or amphiphilic fluoresceins, or DPH (diphenylhexatriene) and DPH derivatives, e.g. TMA-DPH, non-polar BODIPY, like BODIPY Fluorophores or BODIPY FL $C_5$-Ceramide, non-polar pyrene markers and bimane markers, e.g. bimane azide, Lipidtox™ neutral lipid stains, 6-propionyl-2-dimethylaminonaphthalene (Prodan) and Laurdan, dapoxyl derivatives, anilinonaphtalenesulfonate and derivatives thereof. These groups of markers associate to hydrophobic materials, such as cell membranes, and should also function for oil, e.g. lubricating oils. As such, they may be very relevant according to the present invention. It should be mentioned that also other marker groups may be possible to use, such as e.g. fatty acid analogues and for instance phospholipids. Also others are possible according to the present invention.

According to yet another specific embodiment of the present invention, the marker is environmental sensitive and changes the frequency on emitted light depending on the polarity of the surrounding medium. This implies that the colour changes depending on if the surrounding medium is water or oil. In this case you may add the effect of a colour change to the increased intensity described above.

According to yet another specific embodiment of the present invention, the marker is fluorescent and is Nile blue or Nile red, or a combination thereof. Nile blue (or Nile blue A) and Nile red (also known as Nile blue oxazone) are lipophilic stains used in the biology and histology. Both Nile blue and Nile red are environmental sensitive and apart from a colour shift depending on the polarity of the environment the fluorescent intensity is also greatly increased when transferred from a water environment to a non-polar medium. Nile red may be produced by boiling a solution of Nile blue with sulphuric acid. Both are used in conjunction with fluorescence microscopy. According to the present invention, both of the markers are possible to use and function well, however Nile blue may be preferred as Nile red is more expensive than Nile blue. The choice between these markers depends on the application. It may be mentioned that Nile red functions at lower concentrations than Nile blue for many applications, but as Nile red is more expensive, Nile blue is still often a better economical choice.

The invention claimed is:

1. Method for detection of contamination on a surface before performing a coating of the surface, said method comprising bringing a marker into contact with the surface, wherein the marker has an ability of accumulating at a contaminated area on the surface, and detecting the marker on the surface, wherein the marker is non-polar or amphiphilic, wherein the marker is a silicone tracer and the method involves detection of silicone, if present, wherein the marker is fluorescent and is Nile blue or Nile red, or a combination thereof, and wherein the detection of the marker on the surface involves detection of fluorescence performed by applying ultraviolet light.

2. Method according to claim 1, wherein the marker is environmentally sensitive and changes a frequency of emitted light depending on a polarity of a surrounding medium.

3. Method according to claim 1, wherein the marker associates with at least one contaminant present on the surface.

4. Method according to claim 3, wherein association between the marker and the contaminant is driven by a hydrophobic interaction.

5. Method according to claim 1, wherein the coating comprises one or more of a painting technique, a varnishing technique and a covering technique.

6. Method according to claim 1, wherein the surface is a surface of a vehicle.

* * * * *